March 2, 1971 F. L. HIERS Plant Pat. 3,036

GARDENIA PLANT

Filed Oct. 3, 1968

INVENTOR
FRANK L. HIERS
BY Cushman, Darby & Cushman
ATTORNEYS

United States Patent Office

Plant Pat. 3,036
Patented Mar. 2, 1971

3,036

GARDENIA PLANT

Frank L. Hiers, P.O. Box 688, Macclenny, Fla. 32063

Filed Oct. 3, 1968, Ser. No. 764,972
Int. Cl. A01h *5/00*
U.S. Cl. Plt.—54 1 Claim

DISCOVERY OF THE NEW VARIETY

The first specimen of the new gardenia was discovered as a sport or mutant in 1963 in the discoverer's nursery in Manatee County, Fla., in an area in which gardenias of the Ami Yokoskida were under cultivation.

ASEXUAL REPRODUCTION OF THE NEW VARIETY

Succeeding generations of the new variety, consistently having the distinctive characteristics of the first specimen, have been produced by taking cuttings from preceding plants of the new variety.

In the first instance, two mature nodes were taken from the first specimen, the cutting being about three inches in length. The lower end region of the cutting was placed in a rooting medium; roots were produced and the resulting plant flowered, exhibiting the distinctive characteristics of the new variety.

The new variety is now well established, several thousand plants having been grown from cuttings from the first specimen and from subsequent cuttings and are now in flowering production.

THE ATTACHED PHOTOGRAPHIC DRAWING

A specimen of the new variety is depicted in three stages in the attached drawing, wherein.

DETAILED DESCRIPTION

Figure 1:
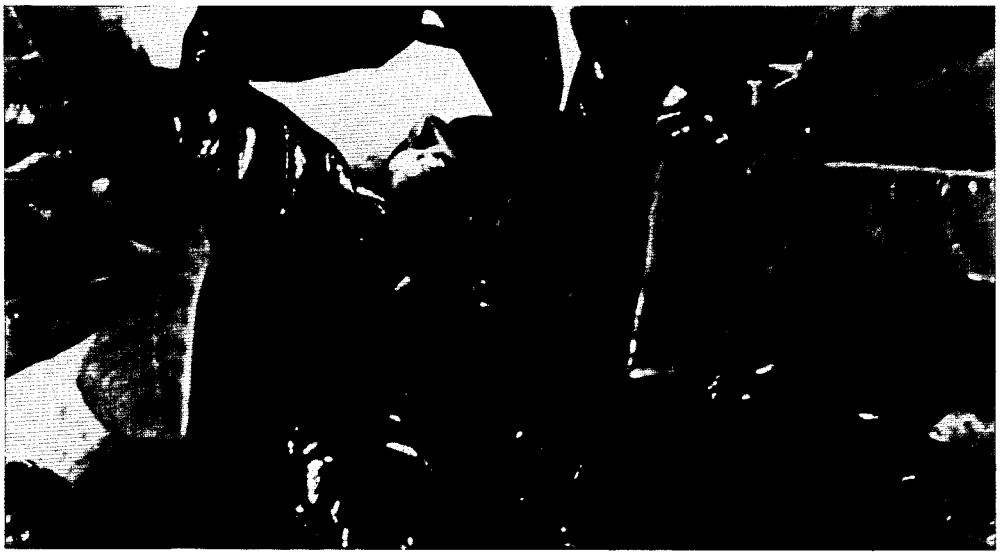
FIG. 1 is a photographic view of the new gardenia showing a bud, just before opening, on new growth.
Figure 2:
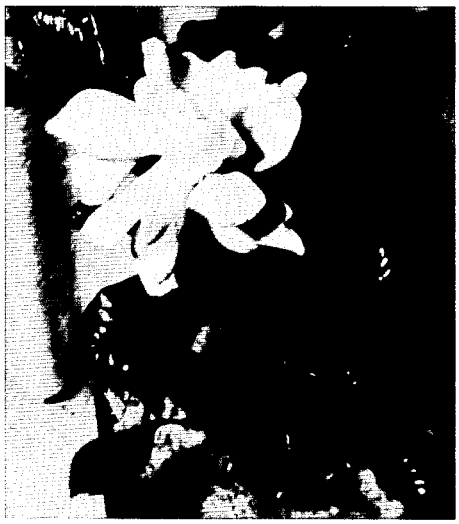
FIG. 2 is a photographic view of the new gardenia, showing a partially open bloom.
Figure 3:
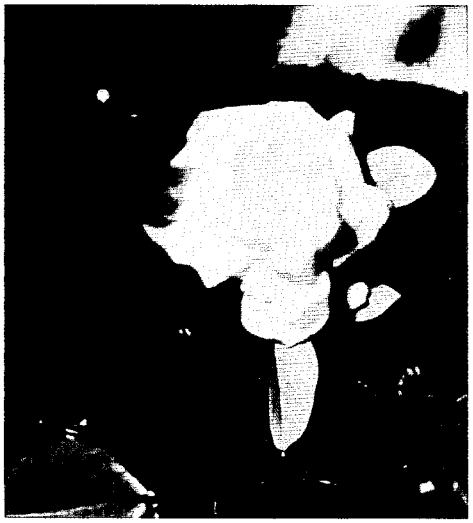
FIG. 3 is a photographic view of the new gardenia, showing a formal double bloom, approximately four to five inches across. Note that the bloom does not show its stamens.

The new gardenia is a sport or mutant originating from the Ami Yokoskida variety of gardenia.

FOLIAGE

The foliage is larger and more attractive than that of the Ami Yokoskida variety.

Leaf texture: Heavy; thicker than the Belmont, Glazieri, Miami Supreme, Veitchii, Rose Bud and most other gardenia foliage. Leaf deeply veined, giving a crinkled effect. Very high gloss.

Leaf size: Between 4½ and 7½ inches long.

Leaf shape: Elliptic, with cuspidate tip and acute base. Leaves are opposite in growth on stem, with leaf margin undulate.

Leaf color: Extremely dark green with soft lighter shading on under side and irradiant veining underneath.

BLOOMING PERIOD

The plant is a heavy producer, producing more blooms than the Belmont, Glazieri, Miami Supreme, Veitchii, Rose Bud and most other gardenias, blooming heavily for approximately 120 days during the months of March, April, May and June; thereafter, blooming lightly over the ensuing months to September 1.

CHARACTERISTICS OF THE BLOOM

Bud: 3 to 4 inches long extremely plump prior to opening. Calyx 1½ to 2 inches in diameter, Peduncle long and heavy. There are 6 loose open sepals which are extra long.

Blossom:

*Size.*—4 to 5 inches in diameter.

*Form.*—Flat but resembling a large rose bloom, petals lie in flat layered rosette and are overlapping.

*Petals.*—Larger than the Belmont, Glazieri, Miami Supreme, Veitchii, Rose Bud and most other gardenias. The petals are 1½ inches in diameter and almost round. Very heavy velvety texture, pure waxy white.

Petallage: Flowers average 30 to 36 petals in 5 to 6 rows.

Fragrance: Exceptionally sweet, with delicate spicy aroma.

Endurance: Does not bruise easily, and lasts longer than the Belmont, Glazieri, Miami Supreme, Veitchii, Rose Bud and most other gardenia varieties. While on the plant, the flower remains white from 8 to 10 days, after which it turns a pure light cream color and remains beautiful for 6 to 8 days longer. When cut, it keeps for approximately 2 weeks.

THE PLANT

Growth: Very vigorous and strong-growing plant, that will double in size under ordinary conditions from year to year, and if given special treatment, will put on 2 to 3 feet of new growth in 6 to 8 months.

Disease: Disease resistant. Free of leaf spot and especially resistant to the two main enemies of gardenias—nematode and white fly. The new variety has been propagated and growth in ordinary untreated soil to date.

Stems: Brown on the hard wood (like Veitchii), strong and sturdy.

What is claimed is:

1. The new and distinct variety of gardenia herein shown and described, identified by the combination of characteristics set forth hereinabove.

References Cited

UNITED STATES PATENTS

P.P. 622 4/1944 Kondo ..... Plants—54

ROBERT E. BAGWILL, Primary Examiner